United States Patent
Ormancey

(10) Patent No.: US 10,966,914 B2
(45) Date of Patent: Apr. 6, 2021

(54) SKIN MIMICKING EMULSION

(71) Applicant: Counter Brands, LLC, Santa Monica, CA (US)

(72) Inventor: Xavier Ormancey, Los Angeles, CA (US)

(73) Assignee: COUNTER BRANDS, LLC, Santa Monica, CA (US)

( * ) Notice: Subject to any disclaimer, the term of this patent is extended or adjusted under 35 U.S.C. 154(b) by 0 days.

(21) Appl. No.: 15/906,600

(22) Filed: Feb. 27, 2018

(65) Prior Publication Data

US 2018/0360717 A1    Dec. 20, 2018

Related U.S. Application Data

(60) Provisional application No. 62/519,670, filed on Jun. 14, 2017.

(51) Int. Cl.
 *A61K 8/55* (2006.01)
 *A61K 8/03* (2006.01)
 (Continued)

(52) U.S. Cl.
 CPC ............ *A61K 8/553* (2013.01); *A61K 8/0295* (2013.01); *A61K 8/03* (2013.01); *A61K 8/19* (2013.01); *A61K 8/342* (2013.01); *A61K 8/345* (2013.01); *A61K 8/361* (2013.01); *A61K 8/365* (2013.01); *A61K 8/37* (2013.01); *A61K 8/375* (2013.01);
 (Continued)

(58) Field of Classification Search
 CPC ........ A61K 8/342; A61K 8/365; A61K 8/553; A61K 8/73; A61K 8/673; A61K 8/676; A61K 8/678; A61K 8/0295; A61K 8/03; A61Q 19/00; A61Q 19/007; A61Q 19/08
 See application file for complete search history.

(56) References Cited

U.S. PATENT DOCUMENTS

| 5,153,000 A | 10/1992 | Chikawa et al. |
| 5,800,818 A | 9/1998 | Prugnaud et al. |

(Continued)

FOREIGN PATENT DOCUMENTS

| GB | 2150433 | 7/1985 |
| WO | 2004075821 | 9/2004 |

(Continued)

OTHER PUBLICATIONS

Mintel, Pure Plant Beauty, "Extra Rich Shea Butter," Jul. 19, 2012, 3 pages.

(Continued)

*Primary Examiner* — Kortney L. Klinkel
(74) *Attorney, Agent, or Firm* — Cislo & Thomas, LLP

(57) ABSTRACT

The present invention is directed to a skin-mimicking emulsion comprised of polyosides, minerals, inositol polyphosphate or phytic acid, polysaccharides, triglycerides, polyols, alpha or beta hydroxy acids, phospholipids, phytosterols, vitamins, fatty alcohols, essential lipids, amino acids, and water. All of the inventive ingredients in combination are design to be similar to those found in skin and are combined to form a lamellar structure for maximum efficacy. The composition does not include any of the components usually found in conventional emulsions, such as synthetic preservatives, surfactants, fragrances, colorants, acrylic polymers, gelling agents, sequestrants, and EDTA as such ingredients would be irritating to the skin.

14 Claims, 4 Drawing Sheets

(51) Int. Cl.

| | | |
|---|---|---|
| A61K 8/73 | (2006.01) | |
| A61Q 19/08 | (2006.01) | |
| A61K 8/365 | (2006.01) | |
| A61K 8/37 | (2006.01) | |
| A61K 8/49 | (2006.01) | |
| A61Q 19/00 | (2006.01) | |
| A61K 8/34 | (2006.01) | |
| A61K 8/67 | (2006.01) | |
| A61K 8/02 | (2006.01) | |
| A61K 8/44 | (2006.01) | |
| A61K 8/19 | (2006.01) | |
| A61K 8/63 | (2006.01) | |
| A61K 8/36 | (2006.01) | |

(52) U.S. Cl.
CPC ............... *A61K 8/44* (2013.01); *A61K 8/498* (2013.01); *A61K 8/55* (2013.01); *A61K 8/63* (2013.01); *A61K 8/673* (2013.01); *A61K 8/676* (2013.01); *A61K 8/678* (2013.01); *A61K 8/73* (2013.01); *A61Q 19/00* (2013.01); *A61Q 19/007* (2013.01); *A61Q 19/08* (2013.01); *A61K 2800/30* (2013.01); *A61K 2800/33* (2013.01)

(56) References Cited

U.S. PATENT DOCUMENTS

| | | |
|---|---|---|
| 5,958,431 A | 9/1999 | Brancq et al. |
| 6,087,403 A | 7/2000 | Bertho et al. |
| 8,388,978 B2 | 3/2013 | Majmudar |
| 8,920,848 B2 | 12/2014 | Gammelsaeter et al. |
| 9,486,401 B2 | 11/2016 | Gammelsaeter et al. |
| 2014/0335136 A1 | 11/2014 | Brieva et al. |
| 2015/0174021 A1 | 6/2015 | Campiche et al. |

FOREIGN PATENT DOCUMENTS

| | | |
|---|---|---|
| WO | 2009106338 | 9/2009 |
| WO | 2012155094 | 11/2012 |
| WO | 2016199976 | 12/2016 |

OTHER PUBLICATIONS

Mintel, Laboratoire NOVExpert, "The Expert Anti-Aging Cream," Jul. 26, 2013, 6 pages.
Mintel, Skin Repair, "Oncology Kit," Oct. 24, 2014, 2 pages.
Mintel, Hermes Arzneimittel, "Cleansing Balm," Oct. 17, 2012, 4 pages.
Mintel, Inaing, "Cell Lotion," Dec. 16, 2014, 5 pages.
European Patent Office, "European Search Report" dated Jan. 23, 2019,15 pages.

SKIN MIMICKING EMULSION

CROSS-REFERENCES TO RELATED APPLICATIONS

This patent application claims priority to provisional Application No. 62/519,670 filed Jun. 14, 2017. This application is incorporated here by this reference.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

TECHNICAL FIELD

This invention relates to skin care compositions and methods of making and applying same. The inventive cosmetic emulsion composition contains a series of different components, all of which are ingredients similar to those found in skin. All of these ingredients find their equivalent in healthy human skin having a function and benefit. This invention has applications in the fields of facial and body care, hair, and complexion.

BACKGROUND ART

Over the last fifty-plus years, the use of skin, body, and hair care products has gradually come to be a daily ritual thanks to the enjoyable feeling and instant comfort it provides, as well as its ease of use and the improvement of skin and hair quality.

This has led to the development of a wide array of products, including emulsions, appearing in different textures and formulations.

Advances in chemistry have made it possible to bring new raw materials to bear, which are more or less natural, to boost cosmetic appeal and provide increased protection for the products in terms of shelf life and preservation of the composition in its intended form.

Many emulsions on the market today are composed of two phases: a water-based phase comprised of water, hydrolysates, aqueous extracts, and the like, and an oil-based phase comprised of oils, waxes, butters, fatty alcohols, and the like, which are emulsified with surfactants. In addition, preservatives, antioxidants, fragrances, colorants, emollients, gelling agents, active ingredients, texturing agents, pigments, solvents, humectants, sequestrants, fillers, and sunscreens may be added. All of these ingredients are essential to the product by forming its color, texture, scent, and impacting its stability as a whole, its preservation over time, and its immediate and long-term cosmetic effectiveness.

Recently, however, some of these ingredients have shown that they are of no use to the skin, and many are harmful to the skin by causing irritation, eliciting an allergic reaction, and interfering with the endocrine system. Chemicals that interfere with the endocrine system may result in developmental malformations, interference with reproduction, increased cancer risk; and disturbances in the immune and nervous system function.

The skin and scalp are living, permeable membranes. Accordingly, there is a risk of some of these raw materials penetrating the skin, altering it, and entering the subcutaneous blood circulation.

Regulations, especially in Europe, have recently sought to prohibit or reduce the use of some of these raw materials for which there is suspicion or proof of risk. Nevertheless, a wide array of ingredients of questionable utility for the skin remain in general use, such as emulsifiers, fragrances, preservatives, gelling agents, and colorants.

Their continued use stems from the necessity to maintain the structure of emulsions, preserve them, stabilize them, and maintain the sensory perception of the product in touch, sight, and smell. Unfortunately, cosmetic products deemed free of these ingredients and "natural" present the same flaws since they are based on the same principles.

Therefore, there is a real need for facial, body, and hair care products that alleviate these flaws, drawbacks, and obstacles of the prior art, especially a formulation approach making it possible to reinvent the manner in which ingredients that are perfectly suited and useful to the skin are selected and combined, while discarding any ingredients that are of no use to it.

DISCLOSURE OF INVENTION

The present invention provides a skin care formulation that forms a lamellar composition comprised of ingredients similar to those found in healthy skin and avoids raw materials that are harmful to the skin. As such, the inventive formulation mimics the skin and enhances the healthy function thereof.

Consequently, the inventive cosmetic composition is comprised of phospholipids and a series of other components consisting of active ingredients directly inspired by molecules related to skin function or structure. Phospholipid levels vary between 0.2-8.00% and the levels of active ingredients (not including water) can vary between 15-50%.

The active ingredients are preferably made up of at least one component from each of the following categories (with its functional or structural equivalent in the skin): polysaccharides in the range of between 0.05-2.00%, lipids (in the form of vegetable oil, fatty alcohol or ester), amino acids or peptides in the range of between 0.05-3.00%, sterols or polyols, triglycerides, antioxidants, mineral salts or trace elements, Vitamins, Natural Moisturizing Factor (NMF), and Squalane.

The pH can be adjusted by adding Alpha or Beta Hydroxy acids, or more specifically, salicylic or lactic acid. Preferably, the pH of the composition is between 4 and 8, and preferably similar to the pH of the skin between 5.0 and 6.0, or around 5.5.

A sample composition comprising the above ingredients is shown in the table below:

| FORMULA INGREDIENT | DERIVED FROM (EXAMPLE) | ACTS LIKE (similar to what element in skin) | FUNCTION (what it does in skin) | BENEFIT |
|---|---|---|---|---|
| Polyosides | *Aloe vera* | skin cell constituent | cell metabolism/ energy | energizing |

-continued

| FORMULA INGREDIENT | DERIVED FROM (EXAMPLE) | | | |
|---|---|---|---|---|
| Minerals | Aloe vera | Essential elements in skin metabolism | Skin balance | calming |
| Inositol polyphosphate or Phytic Acid | Green rice | metabolic pathways | cell functioning | radiance, breathing |
| water | water | the "life" molecule | skin volume, suppleness | moisture |
| polysaccharides | Xanthan gum | cutaneous polysaccharides | structure/density | film forming/barrier |
| Triglycerides | Palm | sebum lipids | nutrition | nutrition/lubrication |
| Polyol | corn | skin polyols | water quenching | hydration |
| Salicylic acid | Gaultheria | skin acids | cell renewal | anti-aging |
| Phospholipids | Glycine max | Cell membrane lipids | barrier function | protection |
| Phytosterols | Shea butter | sebum sterols | activator | skin roughness |
| Vitamin E | Glycine max | vitamin | anti-oxidant | protection |
| Fatty alcohols | Candelilla wax & coconut | NMF | humectant | hydration |
| Essential lipids | Plum oil | skin lipids | cell cohesion | repair |
| Amino acids | beet roots | skin proteins | protein synthesis | energy |

| FORMULA INGREDIENT | DERIVED FROM (EXAMPLE) | PREFERRED AMOUNT % w/w |
|---|---|---|
| Polyosides | Aloe vera | 0.01-1.00 |
| Minerals | Aloe vera | 0.01-1.00 |
| Inositol polyphosphate or Phytic Acid | Green rice | 0.10-1.50 |
| water | water | 42.0-84.8 |
| polysaccharides | Xanthan gum | 0.05-2.00 |
| Triglycerides | Palm | 0.50-15.00 |
| Polyol | corn | 0.20-10.00 |
| Salicylic acid | Gaultheria | 0.05-0.490 |
| Phospholipids | Glycine max | 0.20-8.00 |
| Phytosterols | Shea butter | 0.04-10.00 |
| Vitamin E | Glycine max | 0.01-2.00 |
| Fatty alcohols | Candelilla wax & coconut | 0.50-8.00 |
| Essential lipids | Plum oil | 0.10-10.00 |
| Amino acids | beet roots | 0.05-3.00 |

BEST MODE FOR CARRYING OUT THE INVENTION

The detailed description set forth below is intended as a description of presently-preferred embodiments of the invention and is not intended to represent the only forms in which the present invention may be constructed or utilized. The description sets forth the functions and the sequence of steps for formulating and applying the invention; however, it is to be understood that the same or equivalent ingredients, formulation methods, and applications may be accomplished by different embodiments that are also intended to be encompassed within the spirit and scope of the invention.

After conducting significant research, the inventor has succeeded in developing a formulation principle and the method for obtaining it for cosmetic emulsions, fulfilling these needs perfectly. This is accomplished by the inventive emulsion composition having a physical structure made of layers, i.e., a lamellar emulsion, which is similar to the layers of skin cells as shown by microscopic pictures of the skin. The inventive lamellar composition is composed exclusively of ingredients similar to those found in healthy skin that are wholly useful to its perfect functioning. Surprisingly, the inventive lamellar composition provides optimal skin affinity of the emulsion as the lamellar structure ensures that skin penetration is very fast, and there is no layer of residual ingredients left on the outer skin as conventional emulsions do.

Consequently, the invention consists of identifying ingredients that are actually beneficial to the skin, combining them using a new approach while discarding any that are of no use or even harmful to skin.

Components that are essential to the skin mimic the skin's makeup. On average, healthy skin includes 70% water, with variable distribution, the hypodermis being the most hydrated, 27% proteins, including carbon, hydrogen, oxygen and nitrogen, as well as amino acids, proteins, hormones and enzymes, 2% lipids, including carbon, hydrogen, oxygen, as well as phospholipids, fatty acids, triglycerides, 0.5% mineral salts, including sodium, magnesium, potassium, iron, copper, zinc, sulphur, phosphorous, iodine, and manganese.

The cutaneous layer of the skin surface is composed of the hydrolipidic film, including sebum, perspiration, water, and lipids. In addition to water, it contains mineral salts, trace elements such as copper, calcium, phosphorus, iron, and magnesium, organic substances such as urea, creatinine, proteins, amino acids, and glycosaminoglycans, polysaccharides and glucose metabolites, lipid triglycerides, lipids and free fatty acids, waxes, squalene, and cholesterol (free and esterified).

The stratum corneum layer of skin is particularly rich in NMF (natural moisturizing factors). The principal molecules are glycerol, urea, amino acids, lactates, sugars.

The surface layers of the epidermis are made up of water, amino acids, polysaccharides, lipids, peptides, proteins (collagens), mineral salts, vitamins, and hyaluronic acid. All of these molecules play a role and have a function in of each of the skin layers.

To ensure it is completely useful to the skin, the inventive cosmetic composition is composed specifically of ingredients like those listed above and does not include the common ingredients used in emulsions to date that are irrelevant to skin care or harmful to the skin. For example, the inventive composition does not include any of the components usually found in conventional emulsions, such as synthetic preservatives, surfactants, fragrances, colorants, acrylic polymers, gelling agents, sequestrants, or EDTA.

While preservatives can destroy germs that are likely to contaminate beauty products, there are certain harmful preservatives that are commonly used in skin care products are also absent from the inventive formulation. For example, the inventive compositions are free from parabens, methylisothiazolinone (MIT), phenoxyethanol, benzyl alcohol, and formalin precursors. These ingredients have been shown to be a source of skin reactions and can be endocrine disruptors. To do without them it is necessary to either lower the pH or prevent the water from becoming free and thus susceptible to contamination.

Furthermore, while surfactants such as sulfates, betaines, and polyglucosides can stabilize emulsions and prevent separation of the two phases, they can be irritants since they alter the skin barrier function. For example, it is common for such surfactants to cause contact dermatitis.

Additional components absent from the inventive composition include fragrances, natural or otherwise, as most man-made fragrances and most essential oils contain allergens. Their purpose is to provide a pleasant aroma during application, but the allergens are a source of irritation and skin reactions. Colorants are also absent from the inventive composition as they present the same traits and ideally should be avoided for similar reasons.

Synthetic gelling agents are commonly found in prior art emulsions as they make it possible to adjust viscosity and stabilize the emulsions. However, they are liquid plastics, difficult to biodegrade, film-forming, and vectors for impurities, and therefore, are omitted from the inventive composition.

In addition to the harmful impact all of these common ingredients may have on skin, they should be avoided as they offer nothing to the skin, have no cutaneous benefits, and are a potential source of molecules that are poorly tolerated or irritants. Doing without them is still a huge technical challenge given their important role in the sensory experience of the product, as well as structure and stability during the emulsion.

Advantageously, the inventive composition omits the above ingredients yet still combines together into a structured emulsified medium. In other words, the emulsifiers contained in the inventive composition are organized into a lamellar phase. More specifically, the inventive composition consists of lamellar phases wherein the surfactants are organized into planar bilayers also called lamellae. The bilayers form a periodic stack as they are separated from each other by intermediate layers of water.

Observation with an electronic microscope shows this distribution into lamellae of water- and oil-based phases. This has two effects: limiting the bioavailability of the water (which prevents the proliferation of microorganisms) and giving a "skin feel" touch when applied on the skin.

Consequently, the first object of the invention relates to a cosmetic composition comprised of: phospholipids and a series of other components consisting of active ingredients directly inspired by molecules related to skin function or structure.

According to the invention, it can be used in a form selected from among a fluid emulsion, rich emulsion, serum, or essence for either the face or body. Another object of the invention pertains to a nontherapeutic cosmetic treatment method entailing application on the scalp or hair. Advantageously, application could include a massage to promote assimilation of the product.

In the case of cosmetic methods according to the invention, or use according to the invention, use is understood to mean nontherapeutic use, e.g., for the treatment of healthy skin, that is, skin not presenting a pathological condition.

Advantageously, the variation of the proportion of the ingredients makes it possible to obtain very different viscosities and fluidities. It can even be sprayable, e.g., for a solar product or lotion. It is the organization into a lamellar structure that provides these diverse properties.

This distribution facilitates the application on the skin but also the keratin structures of large surfaces.

Advantageously, the composition of the invention has a high content of active ingredients that allows for easy distribution of a lower dose of the composition compared to conventional prior art compositions.

The inventive emulsion packaging system could be an airless pump tube, single-dose receptacle, a spray, a roller ball applicator, or an airless jar.

Advantageously, the scent of the emulsions is the same as its components.

In the inventive composition, phospholipid levels vary between 0.20-8.00%. Preferred phospholipids include, but are not limited to, lecithin, lysolecithin, hydrogenated lecithin, phosphatidylcholine, *Carthamus tinctorius* oleosomes, and *Prunus amygdalus dulcis* oleosomes.

The levels of active ingredients (not including water) can vary between 15-50%.

The active ingredient is preferably made up of at least one component from each of the following categories (with its functional or structural equivalent in the skin) in proportions similar to those found in healthy human skin: polysaccharides, lipids (in the form of vegetable oil, fatty alcohol or ester), amino acids or peptides, phytosterols or polyols, triglycerides, antioxidants, mineral salts or trace elements, Vitamins, and squalene.

Sample polysaccharides include, but are not limited to, xanthan gum, pullulan, *Sclerotium* gum, *Caesalpinia* gum, *Acacia senegal* gum, xylitol, sodium hyaluronate. Preferred amounts of polysaccharides vary between 0.05-2.00%.

Sample lipids (in the form of vegetable oil, fatty alcohol or ester) include, but are not limited to, *Prunus domestica* seed extract, $C_{12-16}$ alcohols, behenyl alcohol, palmitic acid, hydrogenated vegetable oil, *Macadamia integrifolia* seed oil, *Helianthus annuus* (sunflower) seed oil. Preferred amounts of lipids vary between 0.10-10.00%.

Sample amino acids or peptides include, but are not limited to, arginine, betaine. Preferred amounts of amino acids vary between 0.05-3.00%.

Sample sterols or polyols include, but are not limited to, *Butyrospermum parkii* (shea) butter, pentylene glycol, methylpropanediol. Preferred amounts of sterols or polyols vary between 0.04-10%.

Sample triglycerides include, but are not limited to, caprylic/capric triglyceride, $C_{10-15}$ triglycerides. Preferred amounts of triglycerides vary between 0.50-15.00%.

Sample antioxidants include, but are not limited to, tocopherol, tocopheryl acetate. Preferred amounts of antioxidants vary between 0.01-2.00%.

Sample mineral salts or trace elements include, but are not limited to, sodium, potassium, calcium, magnesium. Preferred amounts of mineral salts or trace elements vary between 0.01-2.00%.

Sample vitamins include, but are not limited to, Vitamin E, Vitamin F, pro-Vitamin B5, Vitamin C. Preferred amounts of vitamins vary between 0.01-2.00.

The preferred amount of squalane varies between 0.50-5.00%.

The pH can be adjusted by adding Alpha or Beta Hydroxy acids. Sample alpha or beta hydroxyl acids include, but are not limited to, salicylic or lactic acid. Preferred amounts of alpha or beta hydroxyl acids vary between 0.10-10.00%.

Phospholipids, polysaccharides, amino acids, phytosterol or polyols, NMF components, vitamins, mineral salts or trace elements, squalane, anti-oxidants, epidermal lipids must be in the composition.

The composition of the invention can be obtained by any appropriate method known to a person skilled in the art for the composition of a lamellar cosmetic emulsion. For example, it could consist of a classic emulsification process from a premix of each of the water- and oil-based phases. Alternatively, the composition of the invention can be obtained by an appropriate method known to a person with skill in the art. For example, phospholipids can be added to the water phase and hydrolyzed prior to addition of the oil phase for emulsification.

Surprisingly, these compositions have a lamellar structure similar to the lamellae found in the various skin layers. Instead of the common dispersion on the skin of one phase in another in the form of microdroplets, the spatial organization is in the form of lamellae, which is transferred to the skin at the time of application by a rapid fusion that leaves no residue (skin feel effect), proof of the product's complete affinity with the skin's surface layers.

The main end benefit of this novel type of composition is to enable skin to easily assimilate the elements that it needs to be more healthy and balanced in a manner not available before.

This type of emulsion helps skin adapt to the ever-changing aggressors of modern life, including dryness or humidity, temperature changes, UV, free radicals, pollution, unbalanced diet, lack of rest, and jetlag, by adjusting hydration, nutrition, and oxygenation levels throughout the day. The inventive technology harnesses the properties of plant-derived ingredients to exactly match the structure and composition of skin, giving it precisely what it needs and nothing it does not.

These surprising results are shown by a clinical test that was conducted on 24 people divided in two groups of volunteers, one with dry skin and one oily/combination skin. The participants were aged 25 to 50, and only one application was made in 24 H time.

Half of the face was treated with the skin-mimicking emulsion and the other half with the leading moisturizer of the North American selective market. Hydration measurements were made at regular intervals (3 replicates) on cheeks and forehead with a probe. The equipment to measure hydration levels was a Corneometer® manufactured and sold by Courage & Khazaka. The results of hydration levels are shown in the Table appearing in FIG. 1 and establish immediate improvement upon application of the inventive emulsion composition for any type of skin, i.e., dry, normal, or oily/combination. By contrast, non-lamellar skin care compositions require application of several different compositions according to each skin type that increases sebum and lipids for dry skin, decreases sebum/lipids for oily skin, and balances water levels for normal skin.

As shown in FIG. 1, for people with dry skin, the inventive composition emulsion shows a more long lasting correction of the dryness of the skin, i.e., 24 hours versus 6 hours for the conventional emulsion. Therefore, the graph in FIG. 1 establishes that the ideal hydration level is kept up to 24 hours, with no new product application, versus the non-lamellar emulsion hydration benefits that show a significant decrease in hydration levels after 6 hours and little or no hydration after 12 hours.

For people with oily/combination skin, the skin is maintained in the perfection hydration zone and oiliness is reduced upon use of the inventive composition and it is over-hydrated and oily as a result of application of the prior art emulsion.

In addition to effective skin hydration, additional corrective benefits of the inventive lamellar emulsion include improvement of skin roughness, skin radiance, reduction of fine lines as shown by clinical tests after a few weeks of use.

Advantageously, the inventive lamellar composition can be adjusted to the different types of skin that exist all over the body, including facial skin, skin under and around the eyes, skin on the hands and palms, the scalp, the décolletage, feet, heels, and other areas of the body, in order to provide the most suitable benefits.

Still other advantages could appear, to a person with skill in the art, when reading the examples below, illustrated by the attached figures provided for demonstration purposes.

As the composition is made of useful ingredients for the skin, and without texturing or sensorial effect ingredients, in a proportion similar to the ideal proportion in the skin, the amount of product necessary for perfect hydration is approximately 50% lower than for a conventional emulsion or gel. Also, the corrective effect is long-lasting and does not require a new application. A routine based on the application of several products formulated with this approach (for example, a cleansing milk, eye cream, day cream, and night cream) will be synergistic in that less product will be needed upon application, less applications will be needed, and the corrective effect will last a very long time. The inventive composition can be applied after cleaning the skin, usually on dry skin, and will have the long lasting, intensified effect described.

The structure of this emulsion can be verified by any method known to a person skilled in the art, such as microscopy, for example. These compositions also have an analytical profile similar to, if not identical to, that of the components in healthy skin. This can be verified by a person skilled in the art by using the Raman spectroscopy analytical technique, for example. This analysis makes it possible to confirm that the absorption bands of these compositions are similar to those found in skin.

FIG. 2 shows an Electronic Microscope picture of the inventive emulsion having a lamellar structure versus the prior art emulsion shown in FIG. 3 having a totally different, bubbled structure of microdroplets.

FIG. 4 shows a comparison of Raman profiles of the healthy skin and the inventive emulsion showing very similar peaks and analytically confirming similar compositions. The lines in FIG. 4 provide mean group spectra and discriminant features. As shown, the inventive emulsion composition perfectly matches the composition of healthy skin. The dashed line labeled A in FIG. 4 is Group number 1, and the solid line labeled B shows Group number 2.

No functional group that is characteristic of skin is missing and no functional group foreign to it is found there. Advantageously, the composition of the invention does not require the addition of a preservative. This makes it possible to limit or prevent the risk of allergy and irritation.

Advantageously, the composition of the invention makes it possible to forego the use of any undesirable ingredients, or those unnecessary for the skin, that are traditionally used in classic cosmetic emulsions for stabilization, viscosity adjustment, and sensory enjoyment. For example, the inventive composition does not include EDTA, surfactants, including sulfates or ethoxylates (such as PEG), BHT and BHA antioxidants, opacifiers, pigments, mineral fillers, synthetic gelling agents like carbomers (such as acrylic gels), mineral oils, silicones, or synthetic fragrance.

While the present invention has been described with regards to particular embodiments, it is recognized that additional variations of the present invention may be devised without departing from the inventive concept.

DETAILED DESCRIPTION OF THE DRAWINGS

FIG. 1 is a table displaying hydration levels over time of a clinical test that was conducted on 24 people divided in two groups of volunteers, one with dry skin and one oily/combination skin. The horizontal axis 10 of the chart shows hydration Levels from 0 to 20 while the vertical axis 20 shows Time from 0 to 30 hours. Half of the face was treated with the skin-mimicking emulsion and the other half with the leading moisturizer of the North American selective market. Hydration measurements were made at regular intervals (3 replicates at approximately 2, 8, and 24 hours) on cheeks and forehead with a probe. The results of hydration levels for oily skin treated by Classic Emulsion are shown 30. The results of hydration levels for oily skin treated by skin-mimicry are shown 40. The results of hydration levels for dry skin treated by skin-mimicry 50. The results of hydration levels for dry skin treated by Classic Emulsion are shown 60.

Figure 1:
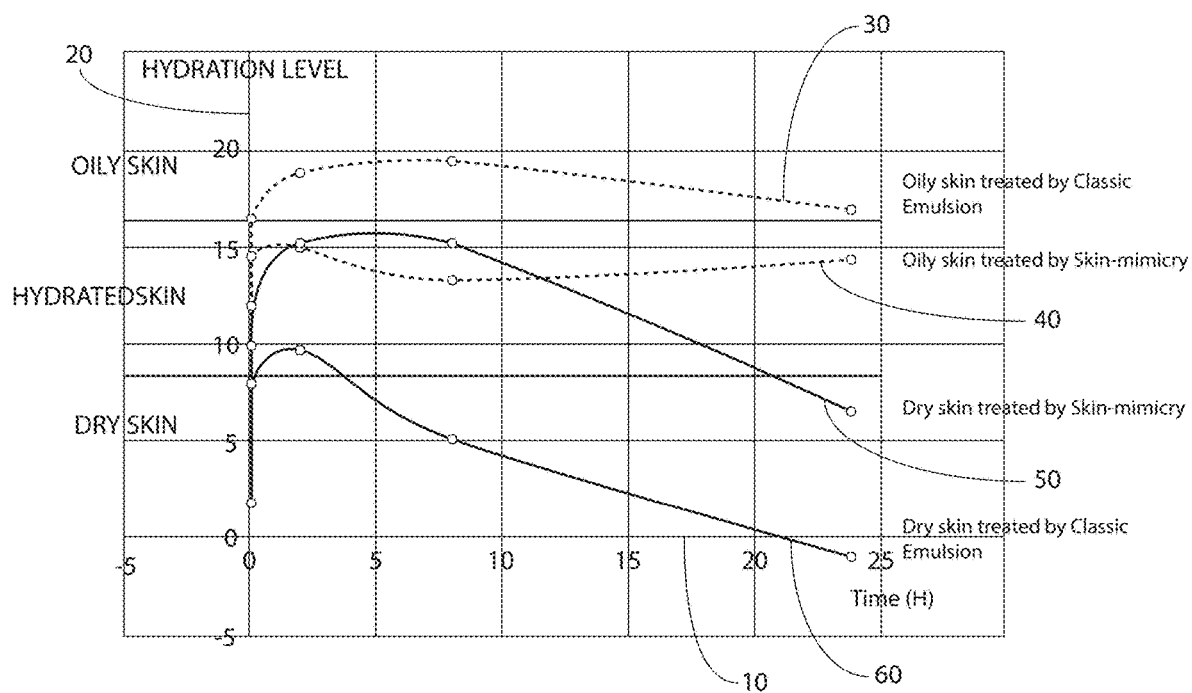
Figure 2:
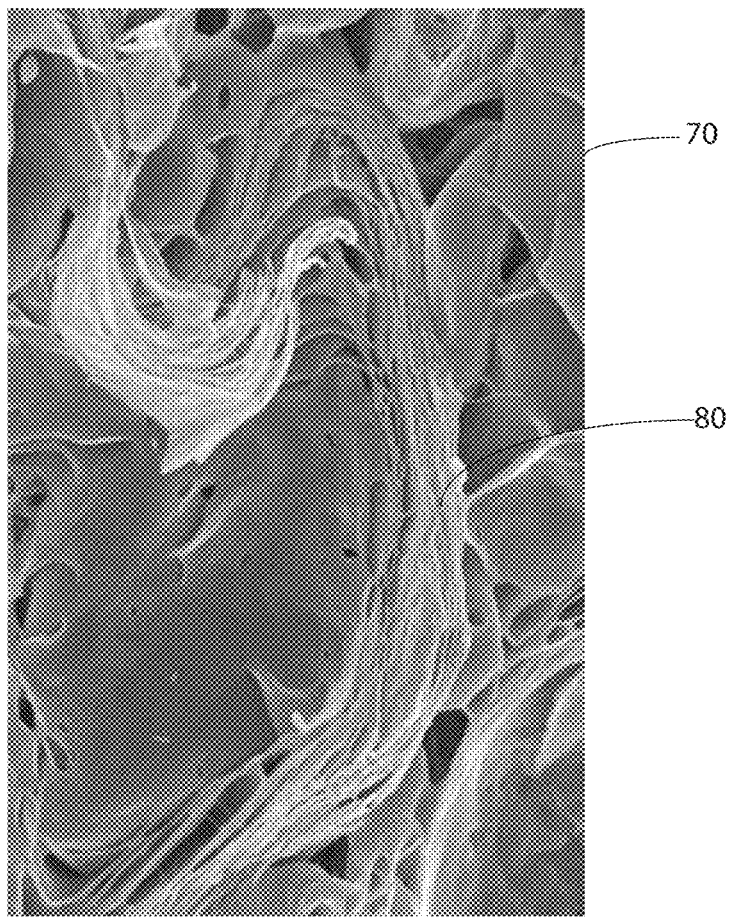
FIG. 2 shows an Electronic Microscope picture 70 of the inventive emulsion having a lamellar structure 80.
Figure 3:
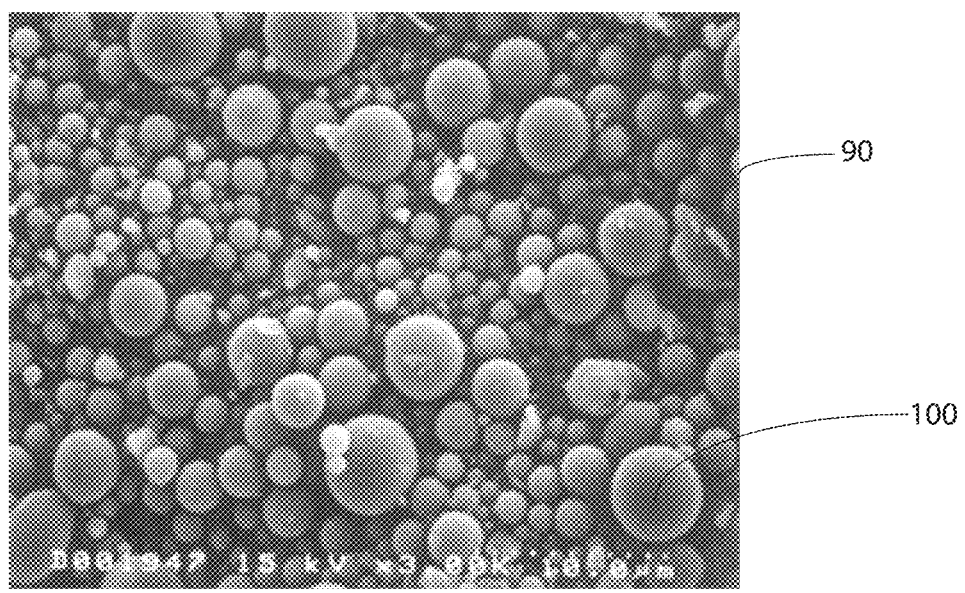
FIG. 3 shows an Electronic Microscope picture 90 of a prior art emulsion having a bubbled structure of microdroplets 100.
Figure 4:
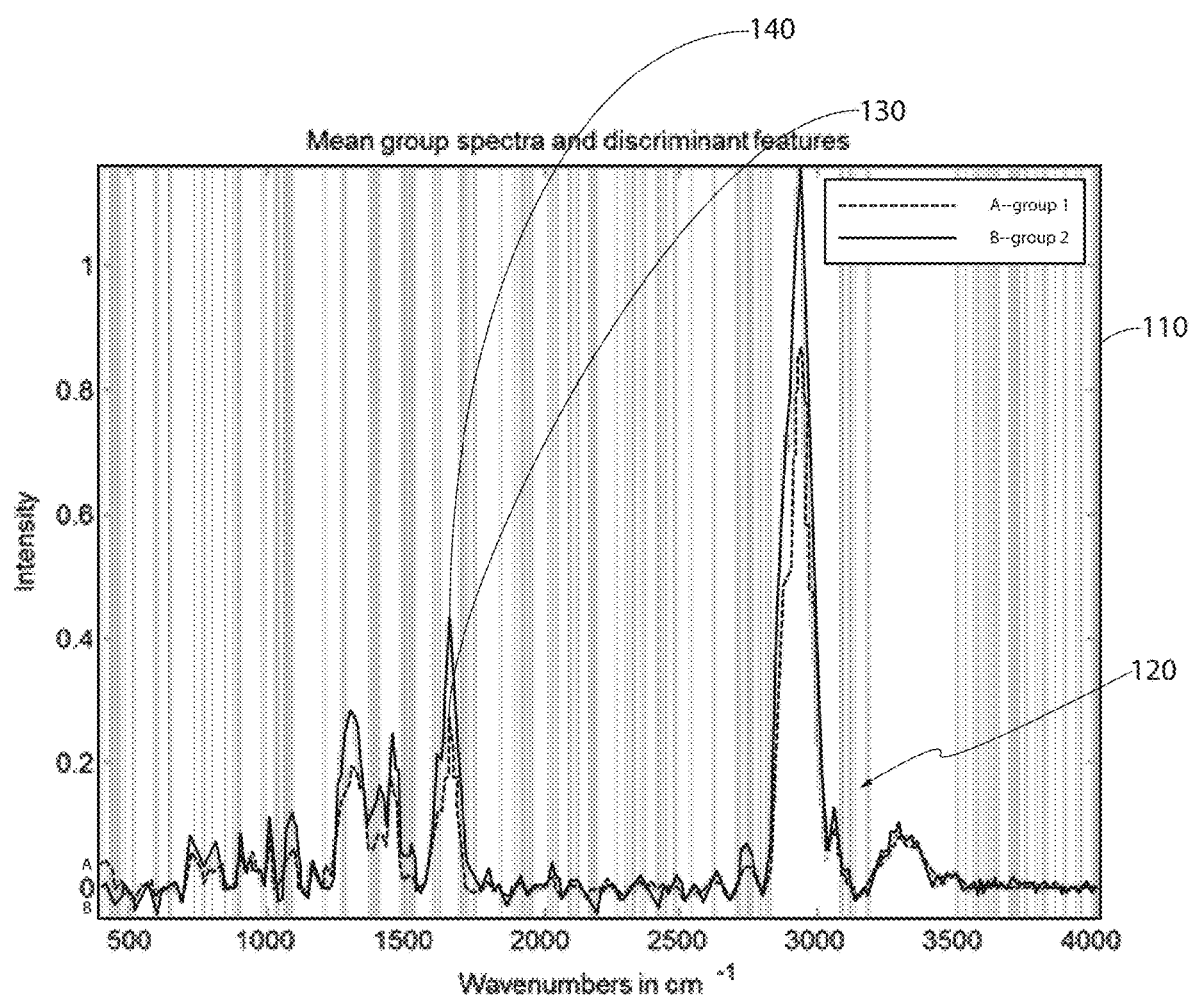

FIG. 4 shows a comparison of Raman profiles of the healthy skin and the inventive emulsion showing very similar peaks and analytically confirming similar compositions 110. The lines in FIG. 4, 120, provide a mean group spects and discriminant features. The dashed line labeled A 130 in FIG. 4 is Group number 1 and the soild line labeled B 140 shows group number 2.

INDUSTRIAL APPLICABILITY

This invention may be industrially applied to the development, manufacture, and use of skin care compositions that mimic human skin.

What is claimed is:

1. A composition comprising polyosides and minerals derived from aloe vera present in a combined total amount of about 0.01 to 1.00% w/w, inositol polyphosphate or phytic acid derived from green rice present in about 0.10 to 1.50% w/w, polysaccharides selected from the group consisting of xanthan gum, pullulan, *Sclerotium* gum, *Caesalpinia* gum, *Acacia senegal* gum, xylitol and sodium hyaluronate present in a combined total amount of about 0.05-2.00% w/w, triglycerides derived from palm present in about 0.50-15.00% w/w, polyols derived from corn present in about 0.20-10.00% w/w, alpha or beta hydroxy acids derived from *Gaultheria* present in about 0.05-0.490% w/w, phospholipids derived from *Glycine max* present in about 0.20-8.00% w/w, phytosterols derived from shea butter present in about 0.04-10.00% w/w, vitamins derived from *Glycine max* present in about 0.01-2.00% w/w, fatty alcohols derived from candelilla wax and coconut present in about 0.50-8.00% w/w, lipids present in about 0.10-10.00% w/w, amino acids derived from beet roots present in about 0.05-3.00% w/w, and water present in about 42.0-84.8% w/w; wherein the composition forms a lamellar structure which is an emulsion made of layers.

2. The composition of claim 1 wherein the phospholipids are selected from the group consisting of lecithin, lysolecithin, hydrogenated lecithin, phosphatidylcholine, *Carthamus tinctorius* oleosomes, and *Prunus amygdalus dulcis* oleosomes.

3. The composition of claim 1 wherein the lipids are selected from the group consisting of *Prunus domestica* seed extract, $C_{12}$-$C_{16}$ alcohols, behenyl alcohol, palmitic acid, hydrogenated vegetable oil, *Macadamia integrifolia* seed oil, and *Helianthus annuus* (sunflower) seed oil.

4. The composition of claim 1 wherein the triglycerides are selected from the group consisting of caprylic/capric triglyceride, and $C_{10}$-$C_{18}$ triglycerides.

5. The composition of claim 1 wherein the vitamins are selected from the group consisting of tocopherol and tocopheryl acetate.

6. The composition of claim 1 wherein the minerals are selected from the group consisting of sodium, potassium, calcium, and magnesium.

7. The composition of claim 1 wherein the vitamins are selected from the group consisting of Vitamin E, Vitamin F, pro-Vitamin $B_5$, and Vitamin C.

8. The composition of claim 1 wherein the alpha or beta hydroxyl acids are selected from the group consisting salicylic acid and lactic acid.

9. The composition of claim 1 wherein the composition does not include synthetic preservatives, synthetic surfactants, synthetic fragrances, synthetic colorants, acrylic polymers, synthetic gelling agents, sequestrants, and EDTA.

10. The composition of claim 1 wherein the composition does not include parabens, methylisothiazolinone, phenoxyethanol, benzyl alcohol, or formalin precursors.

11. A skin care composition comprising a lamellar structure wherein the composition is an emulsion made of layers of surfactants organized into planar bilayers and the bilayers form a periodic stack as they are separated from each other by intermediate layers of water, and wherein the lamellar structure comprises water; polyosides and minerals derived from aloe vera; inositol polyphosphate or phytic acid; xanthan gum; triglycerides; polyol; alpha or beta hydroxyl acids derived from *Gaultheria*; phospholipids; phytosterols; vitamins derived from *Glycine max*; fatty alcohols; lipids; and amino acids.

12. The composition of claim 11 wherein the lamellar structure consists essentially of water; polyosides and minerals derived from aloe vera; inositol polyphosphate or phytic acid; xanthan gum; triglycerides; polyol; salicylic acid; phospholipids; phytosterols; Vitamin E; fatty alcohols; lipids; and amino acids.

13. A method of hydrating skin and improving skin texture comprising topical application of a composition having a lamellar structure consisting essentially of polyosides and minerals derived from aloe vera; inositol polyphosphate or phytic acid; xanthan gum; triglycerides; polyol; salicylic acid; phospholipids; phytosterols; Vitamin E; fatty alcohols; lipids; and amino acids.

14. The method of claim 13 wherein the composition does not include synthetic preservatives, synthetic surfactants, synthetic fragrances, synthetic colorants, synthetic acrylic polymers, synthetic gelling agents, sequestrants, or EDTA.

* * * * *